United States Patent
Isaacson et al.

(10) Patent No.: US 10,525,232 B2
(45) Date of Patent: Jan. 7, 2020

(54) SMART OBTURATOR ASSEMBLY

(71) Applicant: Becton, Dickinson and Company, Franklin Lakes, NJ (US)

(72) Inventors: S. Ray Isaacson, Layton, UT (US); Mark Hunter, Herriman, UT (US); Paul Walker, Sandy, UT (US); Jeff O'Bryan, Murray, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 149 days.

(21) Appl. No.: 15/697,165

(22) Filed: Sep. 6, 2017

(65) Prior Publication Data

US 2019/0070390 A1    Mar. 7, 2019

(51) Int. Cl.
*A61M 25/00*    (2006.01)
*A61B 5/145*    (2006.01)

(52) U.S. Cl.
CPC ..... *A61M 25/0097* (2013.01); *A61B 5/14503* (2013.01); *A61M 2025/0002* (2013.01); *A61M 2025/0073* (2013.01)

(58) Field of Classification Search
CPC ..... A61B 5/14503; A61B 5/01; A61B 5/6852; A61M 2025/0002; A61M 2025/0073; A61M 25/0097; A61M 2025/0018; A61M 2025/0079; A61M 25/00; A61M 2025/0006
See application file for complete search history.

(56) References Cited

U.S. PATENT DOCUMENTS

| | | | | |
|---|---|---|---|---|
| 5,064,415 A | * | 11/1991 | Walder | A61M 25/0017 604/164.02 |
| 2009/0275815 A1 | * | 11/2009 | Bickoff | A61B 5/14532 600/345 |
| 2010/0069855 A1 | * | 3/2010 | Ross | A61M 25/0009 604/268 |

FOREIGN PATENT DOCUMENTS

WO    2011/005814    1/2011

* cited by examiner

*Primary Examiner* — Brandy S Lee
(74) *Attorney, Agent, or Firm* — Kirton & McConkie; Craig Metcalf; Kevin Stinger

(57) ABSTRACT

A smart obturator assembly includes a hub forming a central passage. The hub is configured to couple to a proximal end of a device that forms a lumen such that the central passage is in fluid communication with the lumen. A collar on the hub includes electronic circuitry in signal communication with remote reception circuitry. An obturator is movably positionable within the lumen. The obturator is movable within the lumen between a first position and a second position. The obturator includes a distal end and a sensor at the distal end. The sensor is configured to sense an environmental characteristic within a patient's blood stream, generate a signal representative of the environmental characteristic, and transmit the signal to the electronic circuitry. The electronic circuitry is configured to receive the signal and transmit the signal to the remote reception circuitry.

21 Claims, 7 Drawing Sheets

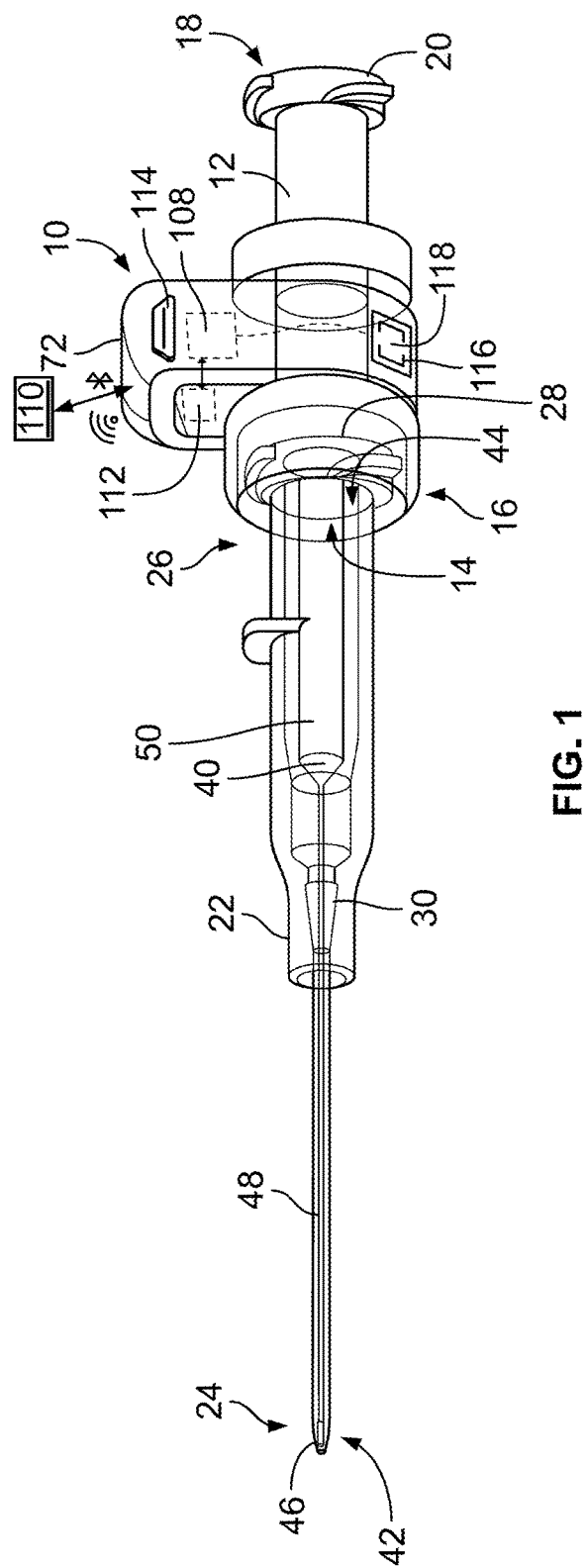
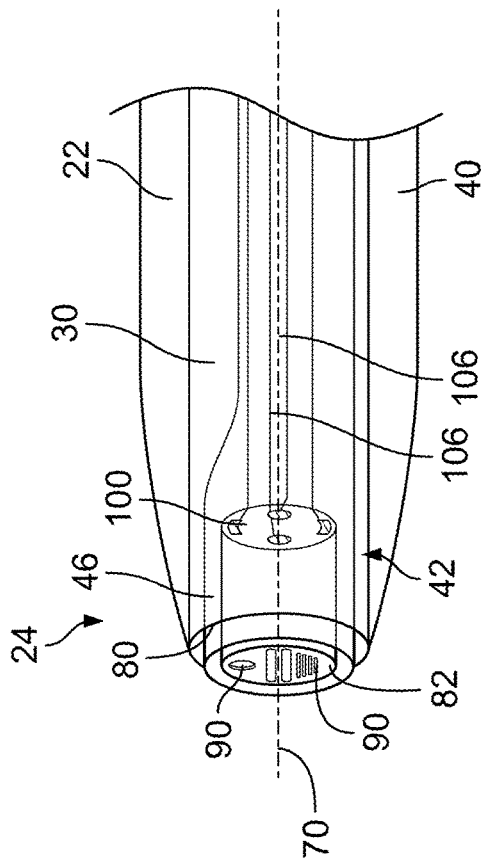
FIG. 1
FIG. 2

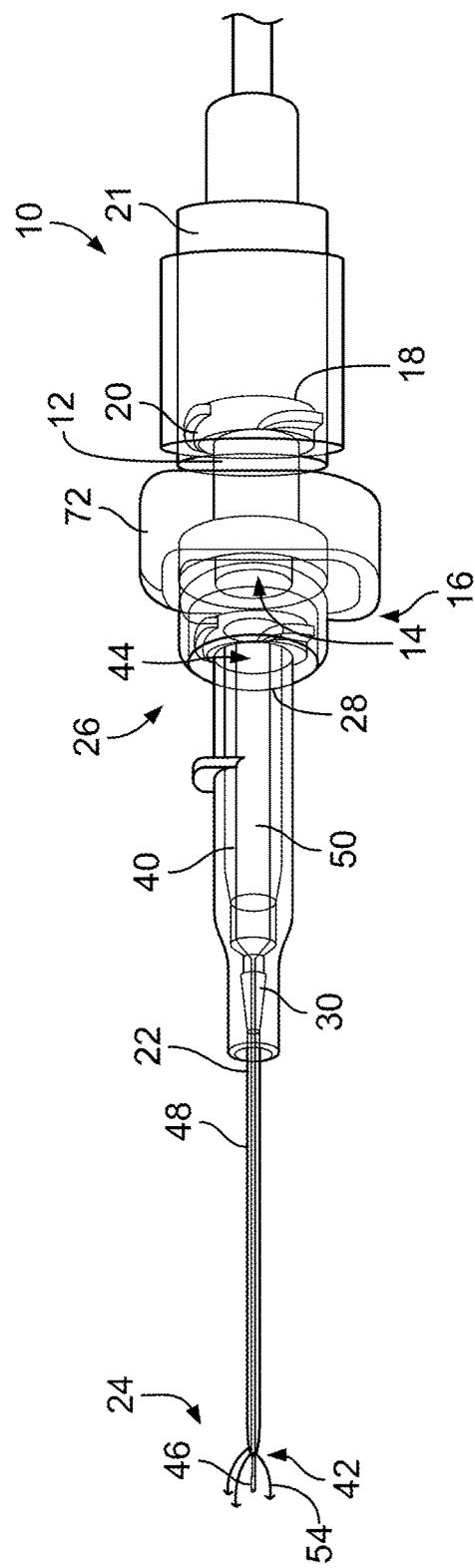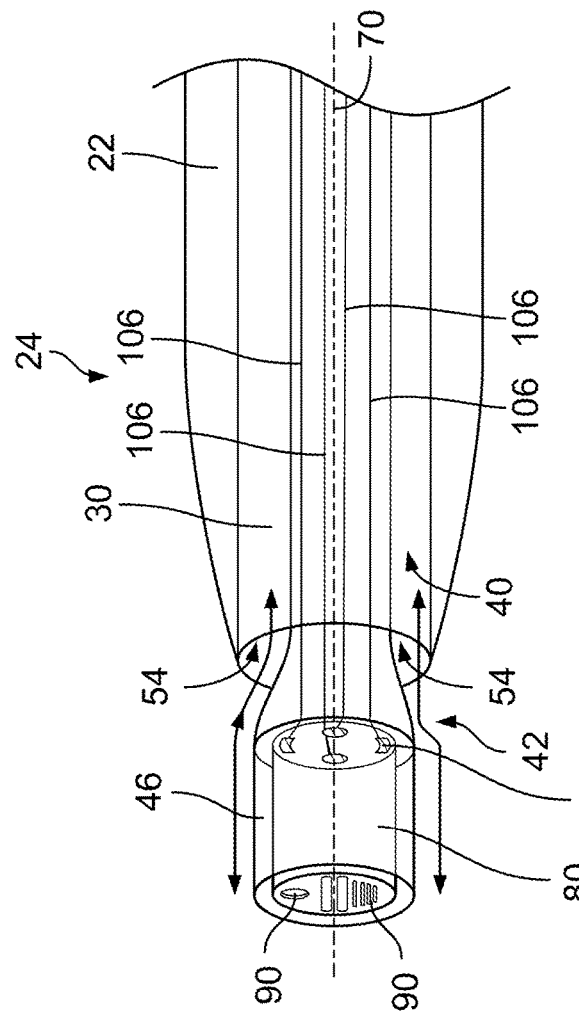

SMART OBTURATOR ASSEMBLY

TECHNICAL FIELD

The present application relates generally to an obturator assembly. More specifically, the present application relates to a smart obturator assembly including an obturator movably positioned within a catheter to selectively control a fluid flow through the catheter and a sensor assembly at a distal end of the obturator to sense environmental characteristics including, for example, different markers, proteins, and/or chemicals in the patient's blood stream.

BACKGROUND

Conventional obturators are utilized to prevent an IV catheter from becoming occluded with clotting blood. If the IV catheter remains open after use, blood can reflux back into the catheter tip and begin to coagulate, obstructing a flow of blood through the tip portion of the IV catheter and preventing continued use of the IV catheter for subsequent therapy. When this happens, the IV catheter must be removed and a replacement IV catheter set to gain vascular access. Bio-films and fibrin can also form over the tip portion of the IV catheter and obstruct blood flow into the IV catheter. In an attempt to prevent this obstruction, some conventional obturators are formed of a solid plastic piece that is inserted from a proximal end of the IV catheter to close or seal the opening of the lumen at the distal end of the IV catheter. The conventional obturator includes an adapter, such as a Luer connector lock, that fits on the proximal end to create a fluid-tight seal, while the distal tip portion of the obturator is positioned in the distal end of the IV catheter to prevent the IV catheter from becoming occluded. Introducing the conventional obturator through the proximal end of the catheter may increase a risk of patient infection.

BRIEF SUMMARY OF SOME EXAMPLE EMBODIMENTS

In one aspect, a smart obturator assembly suitable for use with a device, such as a catheter, includes a hub forming a central passage. An obturator is movably positionable within a lumen of the device operatively coupled to the hub. The obturator is movable within the lumen between a first position and a second position. The obturator includes a distal end having a tip portion and an opposing proximal end and a sensor at the distal end of the obturator. With the obturator in the first position, the distal end limits fluid flow through the lumen and, with the obturator in the second position, the distal end provides fluid flow through the lumen.

In another aspect, a smart obturator assembly suitable for use with a device, such as a catheter, includes a hub forming a central passage. A collar on the hub includes electronic circuitry in signal communication with remote reception circuitry. An obturator is movably positionable within a lumen of the device, wherein the hub is coupled to a proximal end of the device such that the central passage is in fluid communication with the lumen. The obturator is movable within the lumen between a first position and a second position. The obturator includes a distal end and a sensor at the distal end. The sensor is configured to sense an environmental characteristic within a patient's blood stream, generate a signal representative of the environmental characteristic, and transmit the signal to the electronic circuitry. The electronic circuitry is configured to receive the signal and transmit the signal to the remote reception circuitry.

In yet another aspect, a smart obturator assembly suitable for use with a device, such as a catheter, includes an obturator movably positionable within a lumen of the device. The obturator is movable within the lumen between a first position and a second position. The obturator has a distal end and a sensor assembly at the distal end. The sensor assembly is configured to sense one or more environmental characteristics within a patient's blood vessel and to generate one or more signals representative of the one or more environmental characteristics. A hub forming a central passage is coupled to the device such that the central passage is in fluid communication with the lumen. A collar is operatively coupled to the hub. The collar includes electronic circuitry in signal communication with the sensor. The electronic circuitry is configured to receive the one or more signals and transmit the one or more signals to remote reception circuitry.

BRIEF DESCRIPTION OF THE DRAWINGS

FIG. 1 is a perspective side view of an example obturator assembly in a closed fluid flow path configuration according to example embodiments;

FIG. 2 is a partial perspective side view of the example obturator assembly shown in FIG. 1;

FIG. 3 is a perspective side view of an example obturator assembly in an open fluid flow path configuration according to example embodiments;

FIG. 4 is a partial perspective side view of the example obturator assembly shown in FIG. 3;

DETAILED DESCRIPTION

Figure 5:
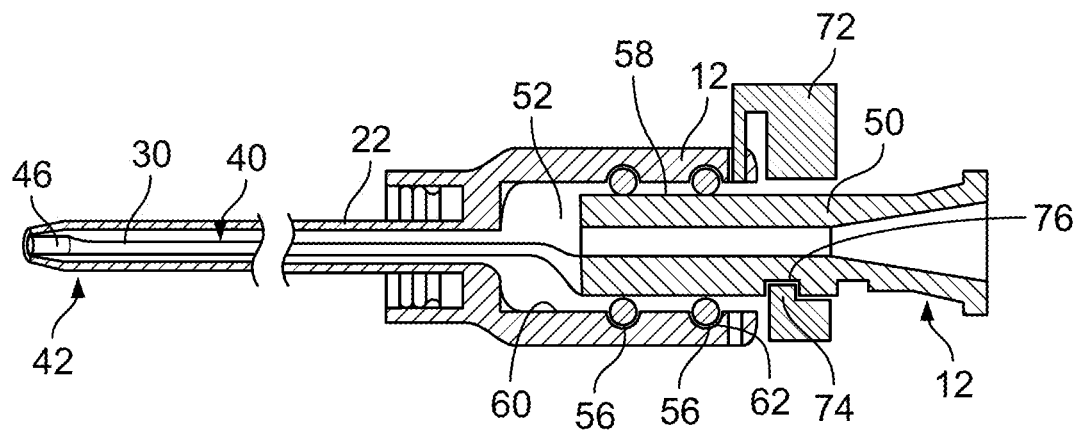
FIG. 5 is a schematic side view of an example obturator assembly in a locked closed fluid flow path configuration according to example embodiments.

Various embodiments are described below with reference to the drawings in which like elements generally are referred to by like numerals. The relationship and functioning of the various elements of the embodiments may better be understood by reference to the following detailed description. However, embodiments are not limited to those illustrated in the drawings. It should be understood that the drawings are not necessarily to scale, and in certain instances details may have been omitted that are not necessary for an understanding of embodiments disclosed herein, such as—for example—conventional fabrication and assembly.

The invention is defined by the claims, may be embodied in many different forms, and should not be construed as limited to the embodiments set forth herein; rather, these embodiments are provided so that this disclosure will be thorough and complete, and will fully convey enabling disclosure to those skilled in the art. As used in this specification and the claims, the singular forms "a," "an," and "the" include plural referents unless the context clearly dictates otherwise. Reference herein to any industry standards (e.g., ASTM, ANSI, IEEE, ISO standards) is defined as complying with the currently published standards as of the original filing date of this disclosure concerning the units, measurements, and testing criteria communicated by those standards unless expressly otherwise defined herein. The terms "proximal" and "distal" are used herein in the common usage sense where they refer respectively to a handle/doctor-end of a device or related object and a tool/patient-end of a device or related object. The terms "about," "substantially," "generally," and other terms of degree, when used with reference to any volume, dimension, proportion, or other quantitative or qualitative value, are intended to communicate a definite and identifiable value within the standard parameters that would be understood by one of skill in the art (equivalent to a medical device engineer with experience in this field), and should be interpreted to include at least any legal equivalents, minor but functionally-insignificant variants, standard manufacturing tolerances, and including at least mathematically significant figures (although not required to be as broad as the largest range thereof).

A smart obturator assembly includes a sensor assembly to provide sensing capabilities for a device, such as an IV catheter, and allow access through the IV catheter. The sensor assembly can provide valuable sensing data for one or more environmental characteristics including, without limitation, temperature, potassium, glucose, sodium, pregnancy testing, drug concentration levels, or any combination thereof. The obturator is selectively movable within the catheter to prevent or limit catheter occlusions and provide a fluid flow path for infusion or aspiration of fluids, for example, without removing the obturator from the catheter lumen.

The smart obturator assembly can be used to access a patient's vein or artery. For example, for application within the artery, the sensor assembly may include a pressure transducer configured to measure and communicate the patient's blood pressure in real time. Conventional methods for measuring a patient's blood pressure in an artery line requires an extension set, setup, maintenance, and flushing. The embodiments described herein will help to eliminate the need for additional tubing, sets, flushing, and maintenance, for example. When used in the venous system, the smart obturator assembly is configured to measure a temperature or potassium, blood glucose, and/or sodium levels, and any combination thereof, for example. If the data shows that a particular therapy is required, the smart obturator assembly is configured to signal the clinician or the pump nearby. The smart obturator assembly may also be used with a patient control dose of pain medicine or with near real-time blood glucose monitoring and automatic dosing of insulin, for example.

In example embodiments, an obturator assembly suitable for use with a device, such as a catheter having a distal end and an opposing proximal end. The catheter forms a lumen extending between the distal end and the proximal end of the catheter. An obturator is movably positionable within the lumen and movable within the lumen between a first position and a second position. The obturator includes a distal tip portion. With the obturator in the first position, the distal tip portion prevents or limits fluid communication and/or fluid flow through the lumen. Conversely, with the obturator in the second position, the distal tip portion provides fluid communication and/or fluid flow through the lumen. The obturator can be locked or secured in the first position or the second position. The obturator is movable in at least one of a distal direction with respect to the distal end of the catheter or a proximal direction with respect to the distal end of the catheter from the first position to the second position. A hub forms a central passage that is in fluid communication with the lumen with the hub coupled to the catheter. A collar is operatively coupled to the hub and is configured in a locked configuration to prevent movement of the obturator within the lumen and in an unlocked configuration to allow movement of the obturator within the lumen. In the locked configuration, the collar is configured to prevent movement of the obturator within the lumen with the obturator in the first position or the second position. The collar may be biased toward the locked configuration with the obturator in the first position or the second position. In example embodiments, at least a portion of the distal end of the obturator has a symmetrical profile with respect to a central axis of the obturator or an asymmetrical profile with respect to the central axis.

The example embodiments described herein provide an obturator to prevent catheter occlusion that is not required to be removed prior to therapy. Rather, the multiple state obturator can be positioned in several states. For example, in a first or closed state, the obturator is configured to close or block a lumen of the catheter to prevent occlusion and/or undesirable reverse blood flow, for example. In a second state, the obturator can be moved within the lumen in a distal direction and/or an opposite proximal direction. Further, the obturator may have a reduced outer diameter in certain embodiments such that when the obturator is advanced, the obturator provides a fluid flow path or fluid opening to allow blood return or fluid infusion. As a result, the obturator does not have to be removed from the catheter lumen; thus, reducing a risk for infection and providing a reliable occlusion prevention mechanism. As described herein, the example multiple state obturator is selectively controllable to prevent or allow fluid flow through the catheter without having to be removed. The obturator assembly can remain installed for the duration of the therapy and provide both an anti-occlusion mechanism and an infusion capability.

In example embodiments, the obturator includes a distal end having a tip portion and an opposing proximal end. A sensor assembly at the tip portion is configured to sense one or more environmental characteristics, generate one or more signals representative of the one or more environmental characteristics, and transmit the one or more signals to a hub or a collar, such as the locking collar of the obturator assembly. In example embodiments, the collar includes electronic circuitry, or a suitable electronic connection coupled in signal communication with the sensor assembly. The electronic circuitry, for example, is configured to receive the one or more signals and transmit or pass-through the one or more signals to remote reception circuitry and/or display a datum representative of the one or more environmental characteristics on a display in the hub, the collar, or another suitable component operatively coupled to the obturator.

As described herein, an example smart obturator assembly includes a sensor assembly having a sensor or an array of sensors at the distal end of the obturator, e.g., at or near the tip portion of the distal end of the obturator and/or at or near the distal end of the catheter. In certain example embodiments, each sensor is positioned within a vein or an artery to directly contact the patient's blood stream. Each sensor is operatively coupled to the electronic circuitry using lead wires that are molded into or are attached to an outside surface or an inside surface of the obturator, for example. In example embodiments, the collar at the proximal end of the obturator assembly is configured with one or more of a variety of electronic and/or communication components to provide power, data transmission, data collection, and data analysis capabilities, as well as other capabilities.

Each sensor may be configured to sense one or more environmental characteristics including, without limitation, different markers, proteins, and/or chemicals in the patient's blood stream. Alternatively, the sensor assembly may include an array of sensor, with each sensor configured to sense one or more environmental characteristics. The sensor assembly may be integrally formed with the obturator or the sensor assembly may be modularized. In certain example embodiments, the obturator provides a socket or a recessed area for housing the sensor assembly. One or more electrical contacts, e.g., one or more conductive pads, are positioned within or near the recessed area for electrical communication with the sensor assembly. For example, two conductive pads electrically couple the sensor assembly and a thermocouple operatively coupled to the collar or the electronic circuitry on or in the collar to sense a temperature. In alternative example embodiments, a wire configuration including a plurality of lead wires may be operatively coupled to the electronic circuitry to provide suitable communication protocols, e.g., USB level communication, which can enable a wide range of sensors, data rates and/or data types on a well-defined BUS. Other suitable communication protocols include, for example, simple plugin, Wi-Fi, Bluetooth® wireless technology, a universal serial bus connector, Radio Frequency Identification (RFID), Near Field Communication (NCF, a derivative of RFID), and self-contained displays. The distal end of the obturator and/or the sensor assembly may be flush with the distal end of the catheter, proud of the distal end of the catheter (i.e., extend past the distal end of the catheter) or recessed into the distal end of the catheter (i.e., proximal to the distal end of the catheter) depending on a desired configuration for a particular sensor or sensor array. The sensor assembly may also provide access through the catheter for in-vivo monitoring as desired.

In certain example embodiments, the obturator assembly has a customizable interface between the obturator and the catheter. This customization may be accomplished with features on the catheter adapter (e.g., a small-bore connector having a 6% tapered fluid connection per International Standard ISO 80369 for liquids and gases in healthcare applications) that must be present in order for the sensor assembly to work properly or with added features. In certain embodiments, a bump, projection, or suitable feature may be present when operatively coupling the obturator to the catheter to sense the bump, projection, or feature and allow the obturator assembly to work properly. As such the obturator assembly can fit properly with catheters having slightly different catheter diameters, lengths, and/or relevant dimensions. Thus, the embodiments described herein may be configured to work properly with various catheters to ensure that the obturator assembly safely and effectively occludes the lumen opening at the distal end of the catheter, as well as provides desired sensing capabilities.

Referring now to the figures, and initially to FIGS. 1-4, an example obturator assembly 10 suitable for use with a device, such as a catheter, having a lumen between a distal end and a proximal end of the device, includes a hub 12 forming a central passage 14 as shown in FIGS. 1 and 3. In example embodiments, central passage 14 extends between a distal end 16 and an opposing proximal end 18 of hub 12. As used herein, the terms "distal" and "distally" refer to a location, a position, and/or a direction situated away from the hub, i.e., a point of origin or attachment, while the terms "proximal" and "proximally" refer to a location, a position and/or a direction situated toward the hub, i.e., the point of origin or attachment. Proximal end 18 of hub 12 is configured to removably couple to any suitable medical device or component, for example, standard medical tubing. As shown in FIGS. 1 and 3, for example, a suitable adapter 20 is formed on or coupled to proximal end 18 to facilitate coupling hub 12 to the medical device or tubing. In certain embodiments, hub 12 includes a small-bore connector configured to couple hub 12 to a medical device or tubing. The medical device or tubing may include a cooperating element 21 shown in FIG. 3, such as a small-bore connector lock, to facilitate coupling the medical device or tubing, for example, to hub 12.

Hub 12 is configured to operatively couple to a device, such as a catheter 22. In example embodiments, catheter 22 has a distal end 24 and an opposing proximal end 26. Catheter 22 may include a cannula extending from a distal end 24 toward an opposing proximal end 26 of catheter 22 in certain example embodiments. At proximal end 26, catheter 22 includes an adapter or body, such as a small-bore connector 28 shown in FIGS. 1 and 3, for example, to couple proximal end 26 of catheter 22 to distal end 16 of hub 12. In certain embodiments, small-bore connector 28 is a small-bore connector having a 6% tapered fluid connection per International Standard ISO 80369 for liquids and gases in healthcare applications. In example embodiments, catheter 22 forms or defines a lumen 30 extending between distal end 24 and proximal end 26 of catheter 22. In example embodiments shown in FIGS. 1 and 3, lumen 30 is in fluid communication with central passage 14 to provide a fluid flow path through obturator assembly 10. In example embodiments, each lumen 30 and central passage 14 has a suitable diameter or a suitable cross-sectional dimension to facilitate fluid flow through obturator assembly 10.

Figure 6:
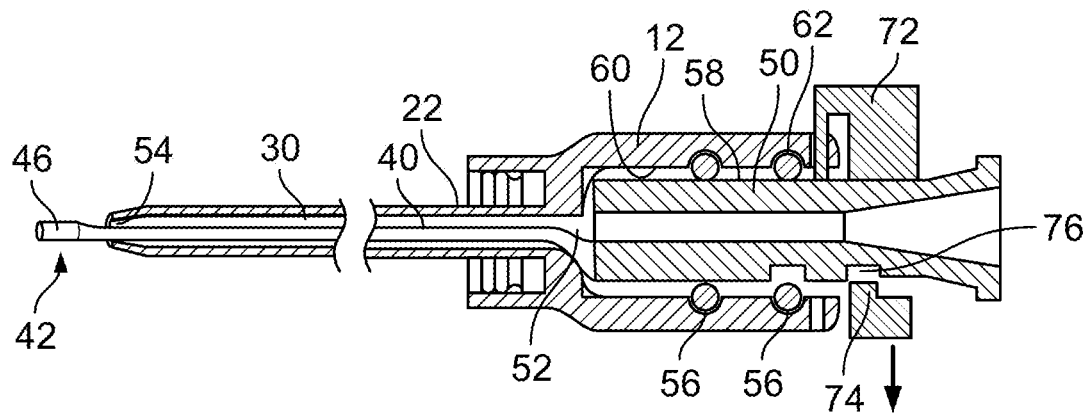
FIG. 6 is a schematic side view of an example obturator assembly in an unlocked open fluid flow path configuration according to example embodiments.
Figure 7:
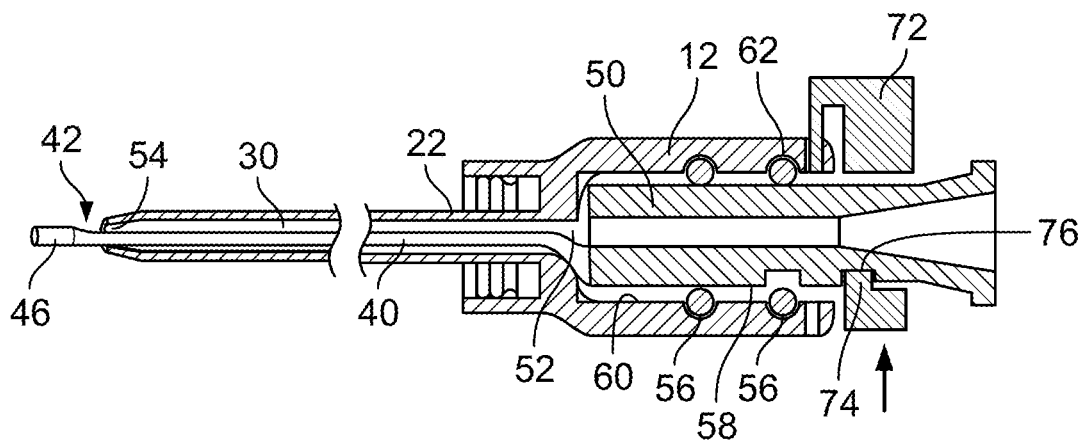
FIG. 7 is a schematic side view of an example obturator assembly in a locked open fluid flow path configuration according to example embodiments.

Referring further to FIGS. 1-4, obturator assembly 10 includes an obturator 40 movably positionable within lumen 30. Obturator 40 is movable within lumen 30 between a first position, such as a closed position shown in FIG. 1, and a second position, such as an open position as shown in FIG. 3. Obturator 40 has a distal end 42 and an opposing proximal end 44. In certain embodiments, obturator 40 includes a tip portion 46 at distal end 42. Tip portion 46 transitions into a body 48 in a midsection of obturator 40 and body 48 transitions into a base 50 at proximal end 44 of obturator 40. In certain example embodiments as shown in FIGS. 5-7, body 48 and/or base 50 forms or defines a channel 52 providing fluid communication between lumen 30 and central passage 14. In example embodiments, with obturator 40 in the first position, distal end 42 and, in certain embodiments, tip portion 46, prevents or limits fluid communication and fluid flow through lumen 30. With obturator 40 in the second position, distal end 42 and, in certain embodiments, tip portion 46, provides fluid communication such that fluid is able to flow through lumen 30 into central passage 14 through channel 52.

In example embodiments, with obturator 40 in the first position, distal end 42, e.g., at least a portion of tip portion 46, is positioned within lumen 30 to prevent fluid flow into lumen 30 and, with obturator 40 in the second position, distal end 42, e.g., at least a portion of tip portion 46, extends from catheter 22 in a distal direction to allow fluid flow into lumen 30. Alternatively, in certain embodiments, with obturator 40 in the second position, distal end 42, e.g., at least a portion of tip portion 46, extends into lumen 30 of catheter 22 in a proximal direction to allow fluid flow into lumen 30. In example embodiments described herein, obturator 40 is movable from the first position to the second position in a distal direction with respect to distal end 24 of catheter 22, i.e., away from hub 12, to extend beyond distal end 24 to provide a fluid flow path 54 as shown, for example, in FIG. 4. Fluid flow path 54 provides fluid communication between lumen 30 and a lumen formed in a vessel, e.g., an artery or vein of a patient in which obturator assembly 10 is positioned. Referring to FIGS. 1-4, in example embodiments, obturator 40 may be used independently of the other components of obturator assembly 10 and/or catheter 22 or may be used with any suitable combination of one or more components of obturator assembly 10 and/or catheter 22.

Referring now to FIGS. 5-7, in example embodiments, a fluid flow in obturator assembly 10, e.g., through at least lumen 30, is selectably controllable. For example, in certain example embodiments, obturator 40 is urged at proximal end 44, e.g., by pushing at base 50 and/or hub 12, to move obturator 40 in a first direction within lumen 30 in the distal direction with respect to distal end 24 of catheter 22 until distal end 42, e.g., at least a portion of tip portion 46, extends distally from lumen 30 of catheter 22 to provide fluid flow path 54 through lumen 30, as shown in FIGS. 6 and 7. Conversely, in these embodiments obturator 40 is urged at proximal end 44, e.g., by pulling at base 50 and/or hub 12, to move obturator 40 in a second direction opposite the first direction within lumen 30 until distal end 42, e.g., at least a portion of tip portion 46 is at least partially positioned within lumen 30 to close fluid flow path 54, as shown in FIG. 5. In certain embodiments, obturator 40 can be moved in the distal direction and the proximal direction using a pump or another suitable device. In alternative example embodiments, obturator 40 is moveable in a proximal direction with respect to distal end 24 of catheter 22, i.e., toward hub 12, from the first position to the second position to extend into lumen 30 a suitable distance to provide a fluid flow path (not shown in the figures). The fluid flow path provides fluid communication between lumen 30 and the lumen formed in the patient's vessel.

Obturator assembly 10 includes one or more seals, such as one or more sleeve seals, formed plastic seals, O-ring seals, or any suitable seals known to those having ordinary skill in the art. In certain embodiments, one or more O-ring seals 56 or other suitable seals or gaskets, positioned about an outer periphery 58 of proximal end 44 of obturator 40 and contacting an inner surface 60 of small-bore connector 28 at proximal end 26 of catheter 22. In certain embodiments, each O-ring seal 56 is positioned within a respective annular slot 62 formed in inner surface 60 of small-bore connector 28 to properly maintain O-ring seal 56 positioned about proximal end 44 of obturator 40 and between obturator 40 and catheter 22 to provide a fluid-tight seal within obturator assembly 10.

Obturator 40 has a central axis 70, shown in FIGS. 2 and 4, extending between distal end 42 and proximal end 44 of obturator 40. In example embodiments, at least a portion of distal end 42, e.g., at least a portion of tip portion 46, has an asymmetrical profile, such as shown in FIG. 2, with respect to central axis 70 or a symmetrical profile, as shown in FIG. 4, with respect to central axis 70. Distal end 42, e.g., at least a portion of tip portion 46, may have any suitable profile that provides the desired fluid flow through fluid flow path 54. In certain conventional obturator assemblies, as a patient's blood is drawn past the distal end of an obturator and into a lumen of the cooperating catheter, shear forces exerted on the red blood cells damage the red blood cells and may tear or rupture the red blood cells causing destruction and disassociation of the red blood cells, sometimes referred to as "hemolysis." Unlike distal ends of conventional obturators, at least a portion of distal end 42 and, particularly, at least a portion of tip portion 46, has a smooth, transitioning profile that facilitates administering or drawing fluids, e.g., blood, to or from the patient while preventing or limiting the damage and destruction of fluid material and the occurrence of hemolysis, for example.

In example embodiments, an amount of fluid flow (i.e., a volume of fluid) through fluid flow path 54 can be optimized by adjusting a cross-sectional area of an opening formed between an outer surface of obturator 40 and an inner wall of catheter 22 forming lumen 30. For example, an outer diameter of obturator 40 and/or an inner diameter of catheter 22 at the distal end of catheter 22 may be adjusted to reduce hemolysis and provide a desired blood sample during a blood draw application. A relatively larger fluid flow path 54 may reduce or eliminate damage to the blood cells during the blood draw. Conversely, an equal amount of fluid flow through a smaller cross-sectional area may provide better infusion performance because the flow is equally divided around the distal end of obturator 40.

As shown in FIGS. 1, 3, and 5-7, in example embodiments, obturator assembly 10 includes a collar, such as a locking collar 72, operatively coupled to hub 12. Locking collar 72 is configurable in a locked configuration, such as shown in FIGS. 5 and 7, to prevent movement of obturator 40 within lumen 30 and in an unlocked configuration, such as shown in FIG. 6, to allow movement of obturator 40 in the distal direction and/or the opposite proximal direction within lumen 30. In the locked configuration, locking collar 72 is configured to retain obturator 40 in a selected position, e.g., the first position or the second position. In FIG. 5, locking collar 72 is in the locked configuration to retain obturator 40 in the first position, e.g., a closed position preventing fluid flow through lumen 30, and prevent obturator from moving from the first position, e.g., to the second position. In FIG. 6, locking collar 72 is in the unlocked configuration to allow obturator 40 to move with respect to catheter 22 in a distal direction or an opposite proximal direction. As shown in FIG. 6, with locking collar 72 in the unlocked configuration, obturator 40 can be moved to the second position, e.g., an open position creating fluid flow path 54 to allow fluid flow into lumen 30. In FIG. 7, with locking collar 72 in the locked configuration, obturator 40 is retained in the second position, e.g., the open position creating fluid flow path 54, and prevented from moving from the second position, e.g., to the first position.

In certain embodiments, locking collar 72 includes a tab 74 positionable within or configured to interfere with a depression 76 formed in obturator 40 with locking collar 72 in the locked configuration. Tab 74 is actuatable to allow locking collar 72 to move between the locked configuration and the unlocked configuration. For example, in example embodiments, tab 74 is depressed to allow locking collar 72 to move from the locked configuration to the unlocked configuration, which allows obturator 40 to move between the first position and the second position. In certain example embodiments, locking collar 72 is biased toward the locked configuration in one of the first position and the second position. More specifically, tab 74 may be biased, using a spring or other suitable biasing member (not shown in the figures), toward the locked configuration in one of the first position and the second position.

Figure 8:
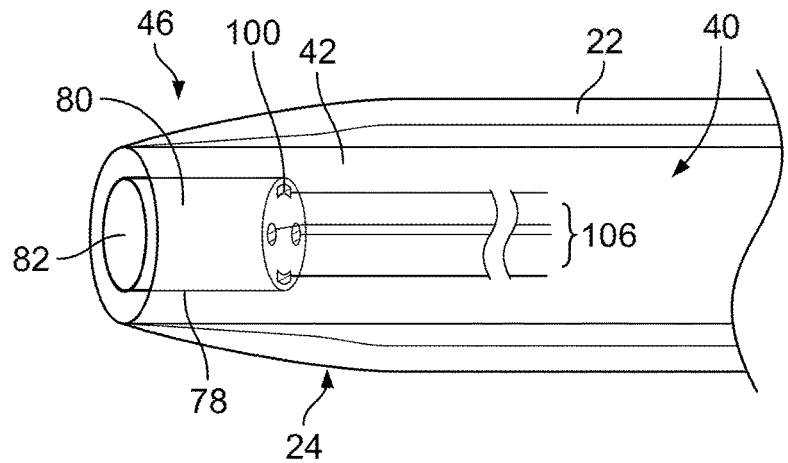
FIG. 8 is a partial perspective side view of an example obturator assembly according to example embodiments.
Figure 9:
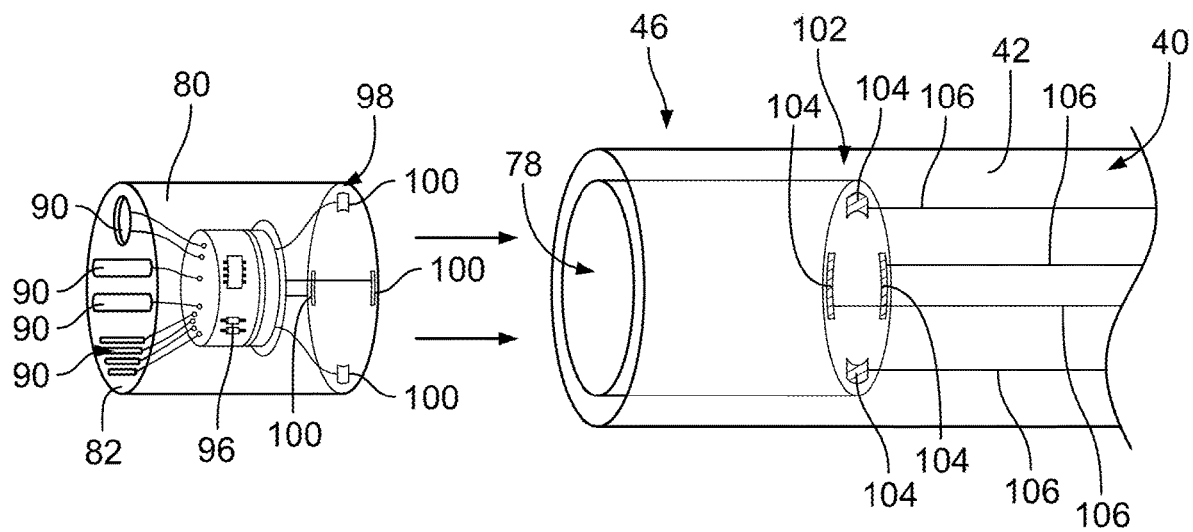
FIG. 9 is an exploded, partial perspective side view of an example obturator assembly according to example embodiments.
Figure 10:
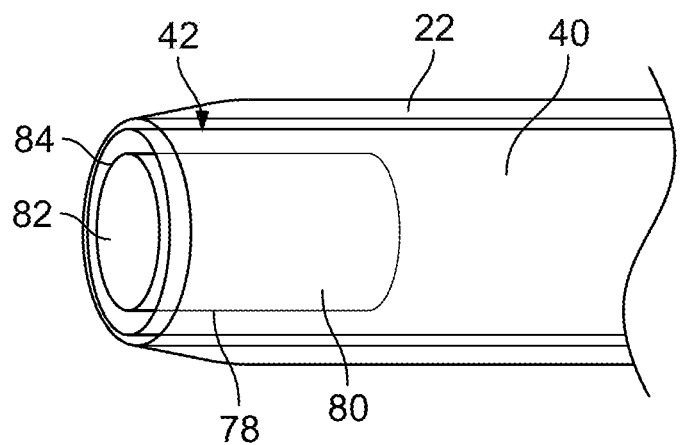
FIG. 10 is a partial perspective side view of an example obturator assembly including a distal end of the obturator flush with a distal end of the catheter according to example embodiments.
Figure 11:
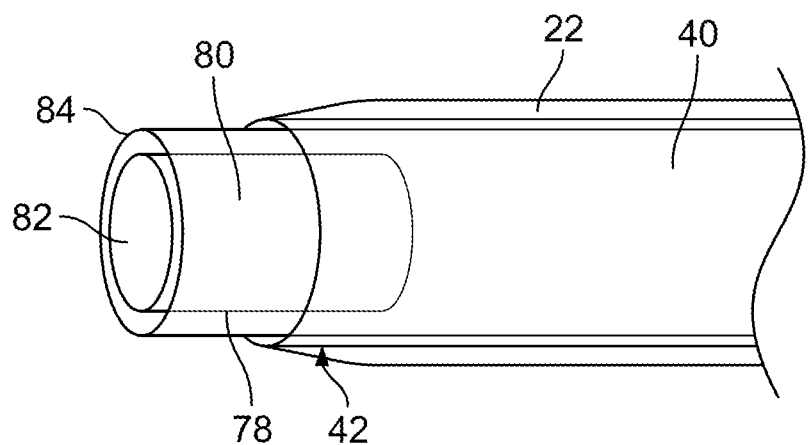
FIG. 11 is a partial perspective side view of an example obturator assembly including a distal end of the obturator proud of a distal end of the catheter according to example embodiments.
Figure 12:
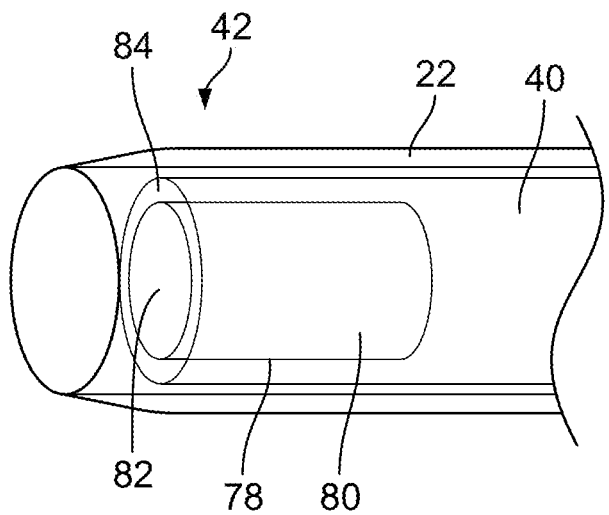
FIG. 12 is a partial perspective side view of an example obturator assembly including a distal end of the obturator recessed in a distal end of the catheter according to example embodiments.
Figure 13:
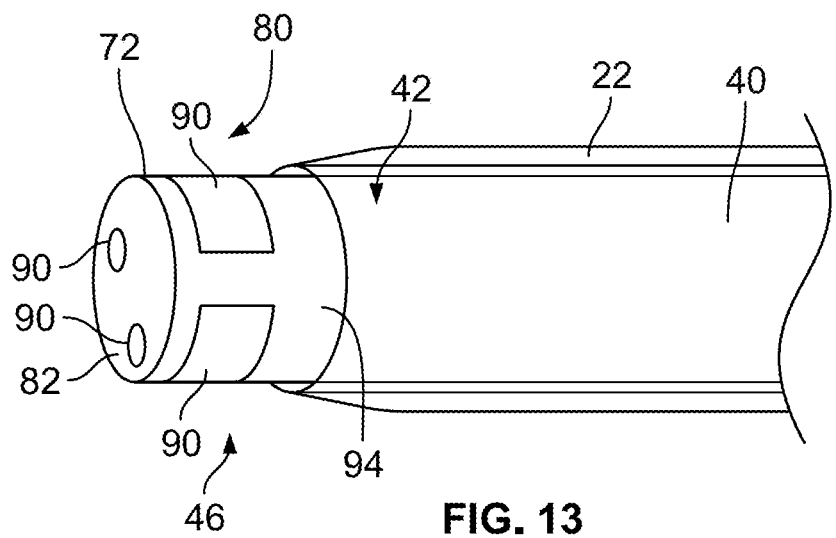
FIG. 13 is a partial perspective side view of an example obturator including a sensor assembly proud of a distal end of the catheter according to example embodiments.
Figure 14:
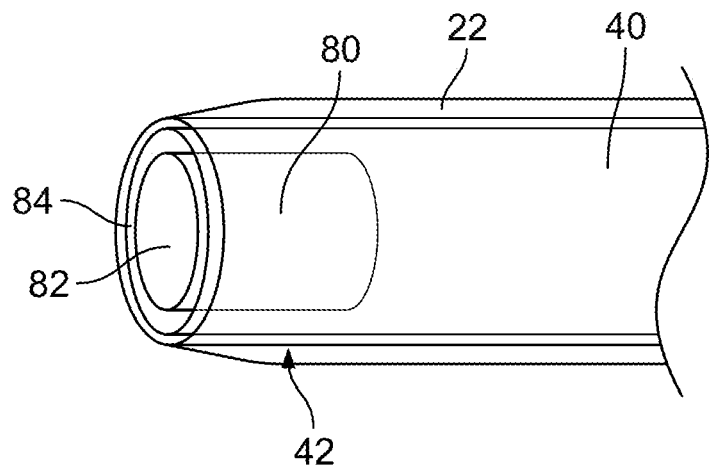
FIG. 14 is a partial perspective side view of an example obturator assembly with a distal end of the obturator flush with a distal end of the catheter according to example embodiments.
Figure 15:
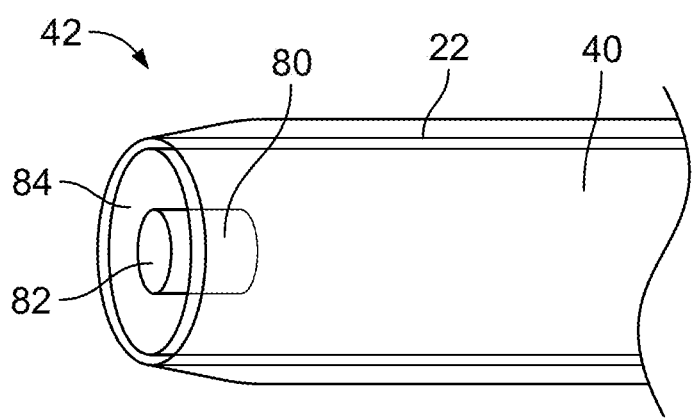
FIG. 15 is a partial perspective side view of an example obturator assembly with a distal end of the obturator flush with a distal end of the catheter according to example embodiments.

Referring further to FIGS. 8-15, in example embodiments, obturator 40 forms a recessed area 78 at distal end 42 of obturator 40. A sensor assembly 80 is positioned at or near distal end 42, e.g., on distal end 42 and/or at least partially within recessed area 78 at tip portion 46. In example embodiments, such as shown in FIGS. 10-12, sensor assembly 80 is positioned within recessed area 78 such that an end surface 82 of sensor assembly 80 is flush with an end surface 84 of obturator 40 at distal end 42. In alternative example embodiments, sensor assembly 80 may be only partially positioned within recessed area 78 such that end surface 82 extends outwardly from end surface 84 of obturator 40 at distal end 42. Referring further to FIGS. 14 and 15, in certain example embodiments, sensor assembly 80 has a constant diameter along a length of sensor assembly 80. An outer diameter of obturator 40 at distal end 42 may vary to properly fit in a lumen of differently-sized catheters, e.g., 14, 16, 18, 20, and 22 gauge catheters. In particular embodiments, the size, i.e., a diameter and/or a length, of sensor assembly 80 is minimized to fit in smaller-sized catheters. Sensor assembly 80 may be coupled to distal end 42 by press-fitting, molding, gluing, snapping, or pinning sensor assembly 80 to distal end 42, for example. Other coupling means known to those skilled it the art may be used to couple sensor assembly 80 to distal end 42.

Sensor assembly 80 is configured to sense one or more environmental characteristics within or related to a patient's blood or blood stream and generate and transmit one or more signals representative of the one or more environmental characteristics. For example, in example embodiments, sensor assembly 80 includes one or more sensors 90, e.g., one sensor 90 or a plurality of sensors 90. Referring further to FIGS. 9 and 13, for example, each sensor 90 is positioned at or on end surface 82 of sensor assembly 90, as shown in FIGS. 9 and 13, and/or positioned on a perimeter surface 94 of sensor assembly 80, as shown in FIG. 13. In example embodiments, each sensor 90 of sensor assembly 80 is configured to measure one or more environmental characteristics including, without limitation, a temperature within a body lumen, a blood glucose level, a sodium level, a potassium level, a drug concentration level, a white blood cell count, a blood pressure within the body lumen, or any combination thereof. Further, sensor assembly 80 may include one or more particular sensors 90 including, without limitation, a temperature sensor, a sensor that senses a chemical within a patient's blood, a sensor that senses a marker in the patient's blood, a sensor that senses a protein in the patient's blood, or any combination thereof.

In example embodiments, sensor assembly 80 includes a plurality of sensors 90, as shown in FIGS. 9 and 13. Each sensor 90 is electrically coupled to, e.g., coupled in signal communication with, an electronic circuit board 96 of sensor assembly 80. A first electrical contact interface 98 including one or more first electrical contacts, such as one or more spring contacts 100, e.g., a plurality of spring contacts, is electrically coupled to, e.g., coupled in signal communication with, electronic circuit board 96. With sensor assembly 80 positioned within recessed area 78, first electrical contact interface 98 is electrically coupled to a second electrical contact interface 102 positioned on and/or in distal end 42 of obturator 40 to electrically coupled second electrical contact interface 102 with sensor assembly 80. Second electrical contact interface 102 includes one or more second electrical contacts, such as one or more contact pads 104. Each contact pad 104 of the one or more contact pads 104 is electrically coupled to a respective spring contact 100 of the one or more spring contacts 100. Referring further to FIGS. 8 and 9, one or more electrical lead wires 106, e.g., a plurality of lead wires 106, extend through obturator 40 to electrically couple, e.g., couple in signal communication, sensor assembly 80 via second electrical contact interface 102 with electronic circuitry 108, operatively coupled to hub 12 and/or locking collar 72, as shown in FIG. 1. In example embodiments, electric circuitry 108 is positioned on and/or within locking collar 72. In certain example embodiments, each electrical lead wire 106 is molded onto tip portion 46 or molded into tip portion 46. Electrical lead wire 106 may extend along a surface of a wall of obturator 40 or may be embedded or molded within at least a portion of a length of the obturator wall between distal end 42 and proximal end 44.

Referring further to FIG. 1, electronic circuitry 108 is configured to transmit or pass-through signals to and receive signals from sensor assembly 80. Electronic circuitry 108 is also configured to transmit signals to and receive signals from remote reception circuitry 110 including an external processor operatively coupled to electronic circuitry 108. Additionally or alternatively, electronic circuitry 108 may be configured to display a datum representative of the one or more environmental characteristics on a display (not shown) on or in hub 12 or on or in locking collar 72, for example. In certain embodiments, communication circuitry 112 in locking collar 72 is electrically coupled to, e.g., coupled in signal communication with, electronic circuitry 108 for wireless communication with remote reception circuitry 110 or an external processor. In these embodiments, communication circuitry 112 includes a radio frequency identification transmitter, a near field communication transmitter, a Bluetooth® wireless technology transmitter, a universal serial bus connector, or any suitable combination thereof. In particular embodiments, a connection port 114, e.g., a USB port, on and/or in locking collar 72 is configured for connecting electronic circuitry 108 with remote reception circuitry 110 or an external processor. Locking collar 72 may also include a compartment 116 housing a power source 118, e.g., a battery pack, as shown in FIG. 1 electrically coupled to electronic circuitry 108 to provide power to electronic circuitry 108 and/or sensor assembly 80. Power supply 118 may be integral to locking collar 72 or externally coupled to locking collar 72.

Locking collar 72, e.g., electronic circuitry 108, may include one or more processors and one or more computer-readable media, one or more communication interfaces, and one or more power sources. The communication interfaces may support both wired and wireless connection to various networks, such as cellular networks, radio, Wi-Fi networks, short range networks (e.g., Bluetooth® technology), and infrared (IR) networks, for example.

Depending on the configuration of electronic circuitry 108, the computer-readable media (and other computer-readable media described throughout) is an example of computer storage media and may include volatile and nonvolatile memory. Thus, the computer-readable media may include, without limitation, RAM, ROM, EEPROM, flash memory, and/or other memory technology, and/or any other suitable medium that may be used to store computer-readable instructions, programs, applications, media items, and/or data which may be accessed by electronic circuitry 108. The computer-readable media may be used to store any number of functional components that are executable on a processor. Electronic circuitry 108 may have additional features or functionality. For example, electronic circuitry 108 may also include additional data storage devices (removable and/or non-removable). The additional data storage media, which may reside in a control board, may include volatile and nonvolatile, removable and non-removable media implemented in any method or technology for storage of information, such as computer readable instructions, data structures, program modules, or other data. In addition, some or all of the functionality described as residing within electronic circuitry 108 may reside remotely from electronic circuitry 108, e.g., in remote reception circuitry 110, in some implementations. In these implementations, electronic circuitry 108 may utilize communication interfaces to communicate with remote reception circuitry 110 and utilize this functionality.

Figure 16:
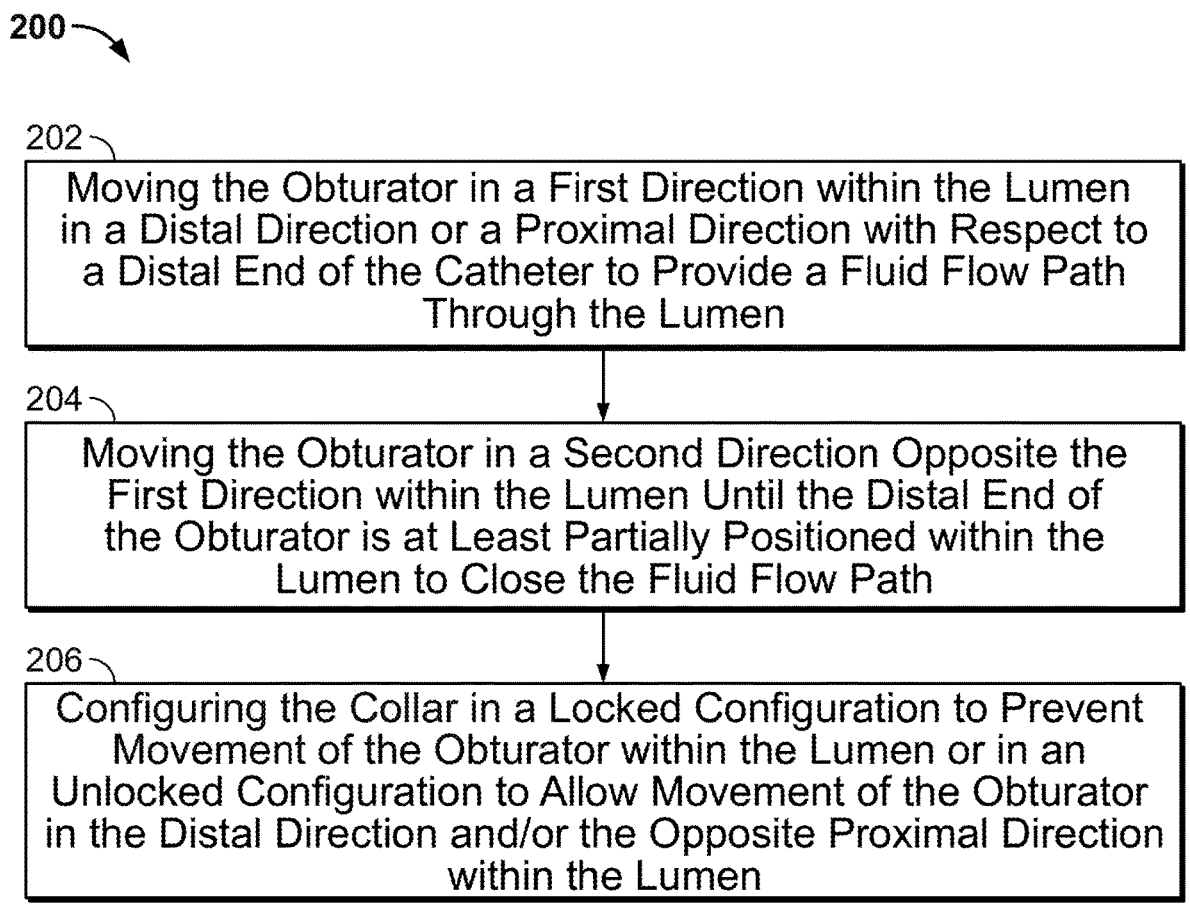
FIG. 16 illustrates steps of an example method for operating an example obturator assembly according to example embodiments.

FIG. 16 illustrates an example method 200 for selectively controlling a fluid flow in an obturator assembly. In example embodiments, the obturator assembly includes a catheter forming a lumen and an obturator positioned within the lumen and movable between a first position and a second position. The method includes moving 202 the obturator in a first direction within the lumen in one of a distal direction and a proximal direction with respect to a distal end of the catheter to provide a fluid flow path through the lumen. Moving 202 may include urging a proximal end of the obturator to move the obturator in a first direction within the lumen in a distal direction with respect to a distal end of the catheter, for example, to provide a fluid flow path through the lumen. As desired, the method also includes moving 204 the obturator in a second direction opposite the first direction within the lumen until the distal end, e.g., at least a portion of the tip portion, of the obturator is at least partially positioned within the lumen to close the fluid flow path. Moving 204 may include urging the proximal end of the obturator to move the obturator in a second direction opposite the first direction within the lumen until the distal end, e.g., at least a portion of the tip portion, of the obturator is at least partially positioned within the lumen to close the fluid flow path.

A collar, such as a locking collar, is operatively coupled to the hub of the obturator assembly. In example embodiments, the method includes configuring 206 the collar in a locked configuration to prevent movement of the obturator within the lumen or in an unlocked configuration to allow movement of the obturator in the distal direction and/or the opposite proximal direction within the lumen. In the locked configuration, the collar is configured to retain the obturator in a selected position, e.g., the first position or the second position. For example, the collar can be positioned in the locked configuration to retain the obturator in the first position, e.g., a closed position preventing fluid flow through the lumen, and prevent the obturator from moving from the first position, e.g., to the second position. The collar can also be positioned in the locked configuration to retain the obturator in the second position, e.g., the open position creating a fluid flow path, and prevent the obturator from moving from the second position, e.g., to the first position. The collar can also be positioned in the unlocked configuration to allow the obturator to move with respect to the catheter in a distal direction or an opposite proximal direction. With the collar in the unlocked configuration, the obturator can be moved between the first position and the second position, for example. In certain example embodiments, the collar is biased toward the locked configuration in one of the first position and the second position. More specifically, a tab of the collar may be biased, using a spring or other suitable biasing member, toward the locked configuration in one of the first position and the second position.

In an example embodiment, a method for selectably controlling a fluid flow in an obturator assembly is provided. The obturator assembly includes a catheter forming a lumen and an obturator movably positioned within the lumen between a first position and a second position. The method includes pushing a proximal end of the obturator to move the obturator within the lumen in a distal direction until a distal tip portion of the obturator extends beyond a distal end of the catheter to provide a fluid flow path. The method further includes pulling the proximal end of the obturator to move the obturator within the lumen in a proximal direction until the distal tip portion of the obturator is at least partially positioned within the lumen to close the fluid flow path.

Those of skill in the art will appreciate that embodiments not expressly illustrated herein may be practiced within the scope of the claims, including that features described herein for different embodiments may be combined with each other and/or with currently-known or future-developed technologies while remaining within the scope of the claims. Although specific terms are employed herein, they are used in a generic and descriptive sense only and not for purposes of limitation unless specifically defined by context, usage, or other explicit designation. It is therefore intended that the foregoing detailed description be regarded as illustrative rather than limiting. And, it should be understood that the following claims, including all equivalents, are intended to define the spirit and scope of this invention. Furthermore, the advantages described above are not necessarily the only advantages of the invention, and it is not necessarily expected that all of the described advantages will be achieved with every embodiment. In the event of any inconsistent disclosure or definition from the present application conflicting with any document incorporated by reference, the disclosure or definition herein shall be deemed to prevail.

We claim:

1. A smart obturator assembly, comprising:
    a hub forming a central passage;
    a catheter extending distally from the hub, wherein the catheter comprises an inner wall forming a lumen; and an obturator movably positionable within the lumen of the catheter operatively coupled to the hub, the obturator movable within the lumen between a first position and a second position, the obturator comprising:
a distal end having a tip portion;
a proximal end opposing the distal end;
a body disposed between the tip portion and the proximal end, wherein an outer diameter of the tip portion is greater than an outer diameter of the body; and
a sensor disposed on a surface of the tip portion, wherein the outer diameter of the tip portion is approximately equal to an inner diameter of a portion of the inner wall, wherein in response to the obturator being in the first position, the tip portion contacts the portion of the inner wall to close the lumen and the sensor either contacts the portion of the inner wall or is disposed distal to the portion of the inner wall,
wherein the obturator in the first position, limits fluid flow through the lumen and, wherein in response to the obturator being in the second position, the body is spaced apart from the portion of the inner wall to provide fluid flow through the lumen.

2. The smart obturator assembly of claim 1, further comprising a locking collar operatively coupled to the hub, the locking collar configurable in a locked configuration to prevent movement of the obturator within the lumen and in an unlocked configuration to allow movement of the obturator within the lumen.

3. The smart obturator assembly of claim 2, wherein, in the locked configuration, the locking collar is configured to prevent movement of the obturator within the lumen with the obturator in the first position or the second position.

4. The smart obturator assembly of claim 2, wherein the locking collar comprises a tab configured to interfere with a depression formed in the obturator with the locking collar in the locked configuration.

5. The smart obturator assembly of claim 2, further comprising electronic circuitry in the locking collar, the electronic circuitry coupled in signal communication with the sensor.

6. The smart obturator assembly of claim 5, further comprising:
an electrical contact positioned within the obturator, the electrical contact electrically coupled to the sensor; and
an electrical lead wire extending through the obturator electrically coupling the electrical contact with the electronic circuitry.

7. The smart obturator assembly of claim 5, further comprising communication circuitry in the locking collar, the communication circuitry coupled in signal communication with the electronic circuitry for wireless communication with remote reception circuitry.

8. The smart obturator assembly of claim 5, wherein the electronic circuitry comprises a connection port for connecting the electronic circuitry with remote reception circuitry.

9. The smart obturator assembly of claim 1, wherein the obturator has a central axis extending between the distal end and the proximal end of the obturator, at least a portion of the distal end having an asymmetrical profile with respect to the central axis.

10. The smart obturator assembly of claim 1, wherein the sensor is configured to measure one or more of the following: a temperature within a body lumen, a blood glucose level, a sodium level, a potassium level, a drug concentration level, a white blood cell count, a blood pressure within the body lumen, or a combination thereof.

11. The smart obturator assembly of claim 1, wherein the hub comprises a small-bore connector configured to couple the hub to a tube.

12. The smart obturator assembly of claim 1, wherein the device comprises a small-bore connector and the proximal end of the obturator forms a channel in fluid communication with the lumen, the obturator assembly further comprising a seal positioned about an outer periphery of the proximal end of the obturator and contacting an inner surface of the small-bore connector at a proximal end of the device.

13. The smart obturator assembly of claim 12, wherein the seal is positioned within an annular slot formed in the inner surface of the small-bore connector.

14. The smart obturator of claim 1, further comprising an electronic circuit board electrically coupled to the sensor, wherein the electronic circuit board is disposed within the tip portion.

15. A smart obturator assembly, comprising:
a hub forming a central passage;
a catheter extending distally from the hub, wherein an inner surface of the catheter comprises a first electrical contact;
a collar on the hub, the collar including electronic circuitry in signal communication with remote reception circuitry; and
an obturator movably positionable within a lumen of the catheter, wherein the hub is coupled to a proximal end of the catheter such that the central passage is in fluid communication with the lumen, the obturator movable within the lumen between a first position and a second position, the obturator comprising:
a distal end; and
a sensor at the distal end, the sensor configured to sense an environmental characteristic within a patient's blood stream, generate a signal representative of the environmental characteristic, and transmit the signal to the electronic circuitry, wherein the electronic circuitry is configured to receive the signal and transmit the signal to the remote reception circuitry;
a second electrical contact at the distal end, wherein the second electrical contact is electrically coupled to the sensor and the first electrical contact; and
an electrical lead wire extending through the obturator electrically coupling the second electrical contact with the electronic circuitry.

16. The smart obturator assembly of claim 15, wherein, with the obturator in the first position, the distal end limits fluid communication through the lumen and, with the obturator in the second position, the distal end provides fluid communication through the lumen.

17. The smart obturator assembly of claim 15, wherein the collar is configurable in a locked configuration to prevent movement of the obturator within the lumen and in an unlocked configuration to allow movement of the obturator within the lumen.

18. The smart obturator assembly of claim 15, further comprising:
communication circuitry coupled in signal communication with the electronic circuitry for wireless communication with the remote reception circuitry; and
a connection port operatively coupled to the electronic circuitry for connecting the electronic circuitry with the remote reception circuitry.

19. A smart obturator assembly, comprising:
an obturator movably positionable within a lumen of a device, the obturator movable within the lumen between a first position and a second position, the obturator comprising:
- a distal end, comprising a tip portion;
- a proximal end opposing the distal end;
- a body disposed between the tip portion and the proximal end, wherein an outer diameter of the tip portion is greater than an outer diameter of the body; and
- a sensor assembly at the tip portion, the sensor assembly configured to sense one or more environmental characteristics within a patient's blood vessel and to generate one or more signals representative of the one or more environmental characteristics;
- an electronic circuit board electrically coupled to the sensor, wherein the electronic circuit board is disposed within the tip portion;
a hub forming a central passage, the hub coupled to the device such that the central passage is in fluid communication with the lumen; and
a collar operatively coupled to the hub, the collar comprising electronic circuitry in signal communication with the sensor, the electronic circuitry configured to receive the one or more signals and transmit the one or more signals to remote reception circuitry.

20. The smart obturator assembly of claim 19, wherein the collar further comprises:
communication circuitry coupled in signal communication with the electronic circuitry for wireless communication with remote reception circuitry; and
a connection port operatively coupled to the electronic circuitry for connecting the electronic circuitry with the remote reception circuitry.

21. The smart obturator assembly of claim 19, wherein the device comprises a catheter having a distal end and an opposing proximal end, the catheter forming the lumen extending between the distal end and the proximal end of the catheter.

* * * * *